(12) United States Patent
Lee et al.

(10) Patent No.: US 10,570,251 B2
(45) Date of Patent: Feb. 25, 2020

(54) ORGANIC ELECTRONIC MULTI-SENSOR USING IONIC ELECTROLYTE, AND METHOD FOR PRODUCING SAME

(71) Applicant: GWANGJU INSTITUTE OF SCIENCE AND TECHNOLOGY, Gwangju (KR)

(72) Inventors: Kwang Hee Lee, Gwangju (KR); Soon Cheol Kwon, Gwangju (KR)

(73) Assignee: GWANGJU INSTITUTE OF SCIENCE AND TECHNOLOGY (KR)

( * ) Notice: Subject to any disclaimer, the term of this patent is extended or adjusted under 35 U.S.C. 154(b) by 0 days.

(21) Appl. No.: 16/317,531

(22) PCT Filed: Jul. 11, 2017

(86) PCT No.: PCT/KR2017/007392
§ 371 (c)(1),
(2) Date: Jan. 11, 2019

(87) PCT Pub. No.: WO2018/012843
PCT Pub. Date: Jan. 18, 2018

(65) Prior Publication Data
US 2019/0233579 A1    Aug. 1, 2019

(30) Foreign Application Priority Data

Jul. 11, 2016  (KR) .................. 10-2016-0087648
Jun. 13, 2017  (KR) .................. 10-2017-0074361

(51) Int. Cl.
*C08G 61/12*       (2006.01)
*H01L 51/00*       (2006.01)
(Continued)

(52) U.S. Cl.
CPC ........... *C08G 61/126* (2013.01); *G01N 27/27* (2013.01); *G01N 27/4141* (2013.01);
(Continued)

(58) Field of Classification Search
CPC .. C08G 61/126; G01N 27/27; G01N 27/4141; H01L 51/0036; H01L 51/0043; H01L 51/0566
See application file for complete search history.

(56) References Cited

FOREIGN PATENT DOCUMENTS

| KR | 20090116652 A | 11/2009 |
|---|---|---|
| WO | 2009119796 A1 | 10/2009 |

OTHER PUBLICATIONS

Cho, Jeong Ho et al., "Printable ion-gel gate dielectrics for low-voltage polymer thin-film transistors on plastic", nature materials, Oct. 19, 2008, vol. 7, Macmillan Publishers Limited.
(Continued)

*Primary Examiner* — Matthew L Reames
(74) *Attorney, Agent, or Firm* — Renaissance IP Law Group LLP (57) ABSTRACT

Provided are: an organic electronic multi-sensor wherein an ionic electrolyte and an organic semiconductor polymer are fused to form a double layer and have a mesh shape; and a method for producing same. The organic electronic multi-sensor provides different, complementary ion and charge transfer pathways depending on the volume ratio of the ionic electrolyte and thus is capable of distinguishing the electrical resistance properties of volatile organic compounds having a wide range of polarities. In addition, the organic electronic multi-sensor senses light of respective wavelengths on the basis of optical signals, converts temperatures to electrical signals according to thermal signals, and thus can sense each environment change.

17 Claims, 10 Drawing Sheets

(51) Int. Cl.
*G01N 27/414* (2006.01)
*G01N 27/27* (2006.01)
*H01L 51/05* (2006.01)

(52) U.S. Cl.
CPC ...... *H01L 51/0036* (2013.01); *H01L 51/0043* (2013.01); *H01L 51/0566* (2013.01); *C08G 2261/124* (2013.01); *C08G 2261/1412* (2013.01); *C08G 2261/18* (2013.01); *C08G 2261/228* (2013.01); *C08G 2261/3223* (2013.01); *C08G 2261/3241* (2013.01); *C08G 2261/3243* (2013.01); *C08G 2261/516* (2013.01); *C08G 2261/94* (2013.01)

(56) References Cited

OTHER PUBLICATIONS

Lee, Jiyoul et al., "Ion Gel Gated Polymer Thin-Film Transistors", Journal of the American Chemical Society, vol. 129, Published on Web Mar. 24, 2007.

Wang, Denjung et al., "Electrolytic Gated Organic Field-Effect Transistors for Application in Biosensors—A Review", electronics 2016, 5, 9, Published Feb. 25, 2016.

ORGANIC ELECTRONIC MULTI-SENSOR USING IONIC ELECTROLYTE, AND METHOD FOR PRODUCING SAME

TECHNICAL FIELD

The present disclosure relates to an organic electronic multi-sensor and a method of producing the same, and more particularly, to an organic electronic multi-sensor formed by fusing an ionic electrolyte with an organic semiconductor polymer, and a method of producing the same.

BACKGROUND ART

For the $4^{th}$ industrial revolution, on the basis of implementation of big data and a hyper-connected society, development of an electronic system capable of collecting information widely is required in place of limited information gathering method depending on vision, auditory, and tactile sensibility of a human being. An electronic nose, an electronic eye, and an electronic skin are devices imitating an olfactory system, a visual system, and a tactile system of a human being and are electronic devices distinguishing and characteristically analyzing odor, light, and temperature. Generally, the electronic nose, the electronic eye, and the electronic skin are terms for a gas sensor, an optical sensor, and a temperature sensor.

The electronic nose is an electronic device which is capable of accurately analyzing a gas. Recently, the need for development of a human welfare type electronic nose capable of analyzing environmental pollution due to volatile organic compounds (VOCs) and accurately detecting and controlling disease diagnosis in real time through respiration is increasing. While a human nose cannot distinguish between different odors in succession, the electronic nose has advantages in that various kinds of odors can be distinguished through a chemical sensor array and even trace amounts of a harmful gas can also be detected.

Generally, an n-type metal oxide semiconductor, such as $TiO_2$, $ZnO$, $SnO_2$, $WO_3$, $CrO_3$, or the like having a band gap of 2.5 eV or more and high charge mobility, is used as a material of the electronic nose. The electronic nose is operated because, when chemical materials, gases, and the like are chemically adsorbed on a surface of a metal oxide semiconductor, electrons move to the surface of the metal oxide semiconductor and thus electrical resistance is changed due to electron depletion.

However, since the resistance reaction due to the gas absorption of the metal oxide semiconductor is amplified by external heat energy, an additional heating device (a Joule heater) is required for a effective operation. The additional heating device has a problem of increasing a volume of the electronic nose device, lowering energy consumption efficiency, and increasing a manufacturing cost.

Therefore, it is required to develop an electronic nose which is operated at room temperature without an additional heating device. Further, in order to cope with an environmental change which is complicated and difficult to analyze, material and element technologies capable of obtaining and analyzing pieces of information on various environmental changes at once are required together with as electronic eye (optical sensor) and electronic skin (temperature sensor).

In particular, organic semiconductors and organic electrolyte materials are gaining attention due to being sensitive to the above-described various environmental changes and having excellent mechanical properties and room temperature driven characteristics.

However, a carbon-based organic material semiconductor and an ionic electrolyte have low charge and low ion mobility characteristics. Further, there is a problem to be solved in that the carbon-based organic material semiconductor is very vulnerable to a polar solvent such as moisture or oxygen due to the nature of the organic material.

DISCLOSURE

Technical Problem

The present disclosure is directed to providing an organic electronic multi-sensor which is capable of being driven at a low voltage, being operated stably for a long period of time, and being applied to a flexible device.

The present disclosure is also directed to providing a method of producing an organic electronic multi-sensor.

Technical Solution

One aspect of the present disclosure provides an organic electronic multi-sensor including: a substrate, a composite layer formed on the substrate and including an ionic electrolyte and an organic semiconductor polymer, and a source electrode layer and a drain electrode layer formed on both sides of the composite layer and electrically connected to the composite layer, wherein the ionic electrolyte may be dissolved in a non-polar solvent and contain a plurality of alkyl groups, the ionic electrolyte may be doped with the organic semiconductor polymer by electrostatic attraction of the ionic electrolyte, and the composite layer may adsorb or desorb gas molecules according to a chemical signal by fusing the ionic electrolyte with the organic semiconductor polymer, detect light per wavelength according to an optical signal, or detect an environmental change by converting a temperature into an electrical signal according to a thermal signal.

The substrate may include a polyethylene terephthalate (PET) substrate having a flexible property.

A precursor of the ionic electrolyte may include 1-methylimidazole, 1-alkyl-3alkyl-imidazolium, n-dialkyl-pyrrolidinium, 1,2-dialkyl-pyrazolum, n-alkyl-thiazolium, n-alkyl-pyridinium, n-diakyl-piperidinium, tetraalkyl-ammomium, tetraalkyl-phosphonium, or trialkyl-sulfonium.

The ionic electrolyte may contain an alkyl group with carbon numbers 1 to 12.

The ionic electrolyte may be either solid or liquid.

The ionic electrolyte may include an anionic material selected from among $PF_6$, $NTf_2$, $BR_1R_2R_3R_4$, $BF_4$, $OTf_2$, $N(CN)_2$, $CH_3CO_2$, $CF_3CO_2NO_3$, Br, Cl, and I.

The organic semiconductor polymer may include a polymer, in which a double bond and a single bond are alternated, selected from among thiophene, fused thiophene, carbazole, benzodithiozole, diketopyrrolopyrrole, and indacenodithiophene.

The composite layer may be fused with a volume ratio of 1:1, 1:2, 1:3, 1:5, 1:7, or 1:10 by increasing the volume ratio of the ionic electrolyte with respect to the organic semiconductor polymer.

The organic electrolyte and the organic semiconductor polymer may simultaneously have different ion and charge transfer systems or may have complementary ion and charge transfer systems.

The composite layer may be formed with a double layer by fusing the ionic electrolyte with the organic semiconductor polymer and may have a mesh shape.

Another aspect of the present disclosure provides a method of producing an organic electronic multi-sensor which includes a substrate, a composite layer formed on the substrate and including an ionic electrolyte and an organic semiconductor polymer, and a source electrode layer and a drain electrode layer formed on both sides of the composite layer and electrically connected to the composite layer, wherein the ionic electrolyte is dissolved in a non-polar solvent and contains a plurality of alkyl groups, the ionic electrolyte is doped with the organic semiconductor polymer by electrostatic attraction of the ionic electrolyte, and the composite layer adsorbs or desorbs gas molecules according to a chemical signal by fusing the ionic electrolyte with the organic semiconductor polymer, detects light per wavelength according to an optical signal, or detects an environmental change by converting a temperature into an electrical signal according to a thermal signal, the method including preparing a precursor of the ionic electrolyte, introducing a functional group into the precursor so as to allow the precursor to be soluble in the non-polar solvent, preparing the ionic electrolyte by chemically bonding the precursor in which the functional group is introduced to an anionic salt, and forming the composite layer by fusing the prepared ionic electrolyte with the organic semiconductor polymer.

In the preparing of the precursor, the precursor of the ionic electrolyte may include 1-methylimidazole, 1-alkyl-3alkyl-imidazolium, n-dialkyl-pyrrolidinium, 1,2-dialkyl-pyrazolum, n-alkyl-thiazolium, n-alkyl-pyridinium, n-diakyl-piperidinium, tetraalkyl-ammomium, tetraalkyl-phosphonium, or trialkyl-sulfonium.

In the introducing of the functional group into the precursor so as to allow the precursor to be soluble in the non-polar solvent, the anionic salt may include an anionic material selected from among $PF_6$, $NTf_2$, $BR_1R_2R_3R_4$, $BF_4$, $OTf_2$, $N(CN)_2$, $CH_3CO_2$, $CF_3CO_2NO_3$, Br, Cl, and I.

In the preparing of the ionic electrolyte by chemically bonding the ionic electrolyte in which the functional group is introduced to the anionic salt, the prepared ionic electrolyte may be in a solid or liquid state.

In the forming of the composite layer, the composite layer may be fused with a volume ratio of 1:1, 1:2, 1:3, 1:5, 1:7, or 1:10 by increasing the volume ratio of the ionic electrolyte with respect to the organic semiconductor polymer.

In the forming of the composite layer, the ionic electrolyte and the organic semiconductor may be fused to form a double layer, and the double layer may have a mesh shape.

The ionic electrolyte may be either solid or liquid.

Advantageous Effects

An organic electronic multi-sensor according to the present disclosure includes a composite layer which is formed by increasing a volume ratio of an ionic electrolyte to an organic semiconductor polymer through a simplified solution process and fusing the ionic electrolyte with the organic semiconductor polymer. In this case, changes are made to a mesh shape of the organic semiconductor polymer and a structure of the ionic electrolyte such that a detection characteristic of the organic electronic multi-sensor can be improved.

Further, the composite layer of the organic electronic multi-sensor of the present disclosure includes complementary ion/charge transfer pathways formed by the fused ionic electrolyte and organic semiconductor polymer such that when gas molecules are absorbed or desorbed, the organic electronic multi-sensor can rapidly convert various kinds of chemical signals into specific distinguishable electrical signals.

Furthermore, the organic semiconductor polymer included in the composite layer of the organic electronic multi-sensor of the present disclosure has a photoelectric characteristic which can be electrically doped by absorbing light such that the organic electronic multi-sensor can rapidly convert an optical signal per wavelength into an electrical signal.

Further, the ionic electrolyte included in the composite layer of the organic electronic multi-sensor of the present disclosure reacts very sensitively to a temperature to vary ionic conductivity such that the organic electronic multi-sensor can rapidly convert a variation in temperature into an electric signal.

Furthermore, an organic electrolyte layer of the organic electronic multi-sensor of the present disclosure forms complementary electron/ion transfer pathways by combining the ionic electrolyte having an alkyl group and the organic semiconductor polymer with electrostatic attraction such that the organic electronic multi-sensor is not provided with a gate electrode and can be driven at room temperature and a low voltage.

Further, an additional heating device is not required for the organic electronic multi-sensor of the present disclosure such that stability of a process can be enhanced and production cost of the process can be reduced.

Furthermore, the organic electronic multi-sensor of the present disclosure can distinguish polar and non-polar volatile organic compound gases.

Further, the organic electronic multi-sensor of the present disclosure can distinguish ultraviolet (UV)/visible (Vis)/near infrared (NIR) wavelength ranges of light.

Furthermore, the organic electronic multi-sensor of the present disclosure can distinguish a variation in temperature.

Further, the organic electronic multi-sensor of the present disclosure can implement a characteristic of low consumption power even in a flexible polyethylene terephthalate (PET) substrate, thereby having high economic feasibility as a next-generation wearable electronic device.

It should be noted that effects of the present disclosure are not limited to the above-described effects, and other effects of the present disclosure not mentioned above can be clearly understood by those skilled in the art from the following descriptions.

DETAILED DESCRIPTION

Hereinafter, exemplary embodiments of the present inventive concept will be described in detail with reference to the accompanying drawings.

The exemplary embodiments of the present inventive concept may be modified in various other forms, and the scope of the present inventive concept is not limited to the exemplary embodiments described below. Further, these embodiments are provided to more fully describe the present inventive concept to those skilled in the art. Therefore, shapes and sizes of components in the drawings may be exaggerated for clarity, and components denoted by the same reference numerals in the drawings are the same components.

Embodiment

Figure 1:
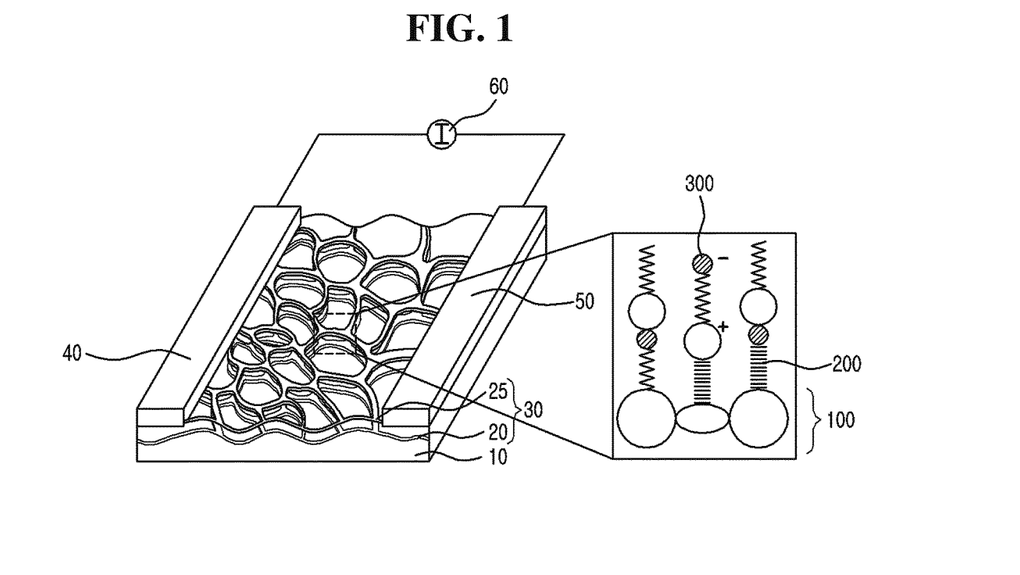
FIG. 1 is a side view of an organic electronic multi-sensor according to one embodiment of the present inventive concept.

FIG. 1 is a side view of an organic electronic multi-sensor according to one embodiment of the present inventive concept.

Referring to FIG. 1, an organic electronic multi-sensor is disclosed.

A substrate 10 is formed. The substrate 10 may be any one selected from among a sapphire ($Al_2O_3$) substrate, a ZnO substrate, a Si substrate, a GaAs substrate, a SiC substrate, an InP substrate, and a GaN substrate, but the present inventive concept is not limited thereto. However, according to the present inventive concept, an organic electrolyte/semiconductor composite layer 30 which is an active layer may be formed by a simplified solution process such that the substrate 10 may include polyethylene terephthalate (PET) which is a flexible element. The substrate 10 may employ a material as long as it can be used as a flexible substrate in addition to PET.

The composite layer 30 including an ionic electrolyte 20 and an organic semiconductor polymer 25 is formed on the substrate 10. The composite layer 30 is formed by fusing the ionic electrolyte 20 with the organic semiconductor polymer 25. The ionic electrolyte 20 and the organic semiconductor polymer 25 are composed of layers having mutually complementary ions and charge transfer characteristics through electrostatic attraction. In this case, the ionic electrolyte 20 may be disposed on or below the organic semiconductor polymer 25. For example, the ionic electrolyte 20 may be disposed on a lower surface of the organic semiconductor polymer 25 or on an upper surface thereof.

The ionic electrolyte 20 may be a solid or a liquid, may be dissolved in a non-polar solvent, and may contain a plurality of alkyl groups. For example, the ionic electrolyte 20 may contain an alkyl group with carbon numbers 1 to 12.

The ionic electrolyte 20 may be doped with the organic semiconductor polymer 25 by electrostatic attraction. The organic semiconductor polymer 25 may include a material, which alternately contains a double bond and a single bond and has anions, such as $PF_6$, $NTf_2$, $BR_1R_2R_3R_4$, $BF_4$, $OTf_2$, $N(CN)_2$, $CH_3CO_2$, $CF_3CO_2NO_3$, Br, Cl, or I.

The composite layer 30 may be a layer which has a new signal transfer system by fusing the ionic electrolyte 20 with the organic semiconductor polymer 25. For example, the composite layer 30 may be fused by increasing a volume ratio of the ionic electrolyte 20 to the organic semiconductor polymer 25 to 1:1, 1:2, 1:3, 1:5, 1:7, or 1:10.

The ionic electrolyte 20 and the organic semiconductor polymer 25 of the composite layer 30 may simultaneously have different ion and charge transfer systems or may have complementary ion and charge transfer systems.

The composite layer 30 may adsorb or desorb gas molecules according to a chemical signal by fusing the ionic electrolyte 20 with the organic semiconductor polymer 25, detect light per wavelength according to an optical signal, and detect an environmental change by converting a temperature into an electrical signal according to a thermal signal. In particular, in the composite layer 30, the ionic electrolyte 20 may be doped with and fused with the organic semiconductor polymer 25 by the electrostatic attraction of the ionic electrolyte 20 to form ion and charge transfer pathways. More specifically, when gas molecules are adsorbed or desorbed on the composite layer 30, electrical resistance of the composite layer 30 may be increased or decreased according to polar and non-polar characteristics. For example, the ionic electrolyte 20 and the organic semiconductor polymer 25 of the composite layer 30 are complementarily fused in ion and charge transfer systems such that the composite layer 30 may efficiently convert a chemical signal into an electrical signal to detect a gas while gas molecules are absorbed or desorbed. Further, due to a photoelectric characteristic, the organic semiconductor polymer 25 of the composite layer 30 may be electrically doped by absorbing light per wavelength such that the composite layer 30 may detect a specific optical signal through the through complementary ion and charge transfer pathways by efficiently converting the specific optical signal into an electrical signal. Alternatively, a structure of the ionic electrolyte 20 of the composite layer 30 may be easily changed due to a temperature and thus an electrical characteristic of the ionic electrolyte 20 is varied such that the composite layer 30 may detect a variation in temperature through the complementary ion and charge transfer pathways by converting the variation in temperature into an electrical signal.

A source electrode layer 40 and a drain electrode layer 50 may be connected to the composite layer 30 and formed on both sides of the composite layer 30. Each of the source electrode layer 40 and the drain electrode layer 50 may be formed of an indium tin oxide (ITO) or Au, but the present inventive concept is not limited thereto. Further, the composite layer 30 is electrically connected to the source electrode layer 40 and the drain electrode layer 50 such that a current 60 may flow.

Hereinafter, a method of producing an organic electronic multi-sensor will be described.

Firstly, a precursor of the ionic electrolyte 20 may be prepared.

The precursor of the ionic electrolyte 20 may be any one of Formula 1.

[Formula 1]

(01)

(02)

(03)

(04)

(05)

(06)

(07)

(08)

(09)

(10)

Formula 1 may include N, P, or S, and R, $R_1$, $R_2$, $R_3$, and $R_4$ may each include an alkyl group. In particular, the precursor of the ionic electrolyte 20 may be one selected from among 1-methylimidazole, 1-alkyl-3alkyl-imidazolium, n-dialkyl-pyrrolidinium, 1,2-dialkyl-pyrazolum, n-alkyl-thiazolium, n-alkyl-pyridinium, n-diakyl-piperidinium, tetraalkyl-ammomium, tetraalkyl-phosphonium, and trialkyl-sulfonium.

Secondarily, a functional group is introduced so as to dissolve the precursor of the ionic electrolyte 20 in the non-polar solvent. The functional group introduced into the precursor of the ionic electrolyte 20 may be an alkyl group with carbon numbers 1 to 12. However, even when a functional group is further introduced, it is preferable that the ionic electrolyte 20 is in a solid or liquid state.

Thirdly, the ionic electrolyte 20 into which the functional group is introduced is chemically combined with an anionic salt to produce the ionic electrolyte 20. In particular, the ionic electrolyte 20 may be doped with the anionic salt. The salt may be an anionic material including one selected from among $PF_6$, $NTf_2$, $BR_1R_2R_3R_4$, $BF_4$, $OTf_2$, $N(CN)_2$, $CH_3CO_2$, $CF_3CO_2NO_3$, Br, Cl, and I.

As described above, the functional group is further introduced into the ionic electrolyte 20 and the ionic electrolyte 20 is doped with the anionic salt such that the ionic electrolyte 20 may be fused with the organic semiconductor polymer 25. For example, a volume ratio of the ionic electrolyte 20 to the organic semiconductor polymer 25 may be increased and fused with the organic semiconductor polymer 25 with the volume ratios of 1:1, 1:2, 1:3, 1:5, 1:7, and 1:10.

The organic semiconductor polymer 25 may be a polymer, in which a double bond and a single bond are alternated, selected from among thiophene, fused thiophene, carbazole, benzodithiozole, diketopyrrolopyrrole, and indacenodithiophene, but the present inventive concept is not limited thereto. However, for an electrostatic interact with the ionic electrolyte, it is preferable that the organic semiconductor polymer 25 is made of a polymer and a monomer, each having an alternating electron donor-acceptor system. For example, the organic semiconductor polymer 25 may be DT-PDPP2T-TT.

As described above, the ionic electrolyte 20 and the organic semiconductor polymer 25 may be fused with each other to be formed as a double layer on the composite layer, and the double layer may have a mesh shape. Further, when the ionic electrolyte 20 and the organic semiconductor polymer 25 are fused, the mesh shape of the composite layer 30 may be varied according to the volume ratio of the ionic electrolyte 20 contained in the composite layer 30. For example, when the ionic electrolyte 20 and the organic semiconductor polymer 25 are fused and the volume ratio of the ionic electrolyte 20 is increased, an inner diameter between meshes of the double layer of the composite layer 30 may be increased.

A signal mechanism of the composite layer 30 will be described below.

A charge transfer pathway 100 and an ion transfer pathway 300 may be disposed by electrostatic attraction 200. For example, the charge transfer pathway 100 may be constituted with the organic semiconductor polymer 25, and the ion transfer pathway 300 may be constituted with the ionic electrolyte 20. The charge transfer pathway 100 and the ion transfer pathway 300 may have a mesh shape by the electrostatic attraction 200.

Further, owing to electrostatic forces between anions and cations of the ionic electrolyte 20 in the composite layer 30 formed on the substrate 10, the organic semiconductor polymer 25 may be electrochemically doped to increase or decrease electrical resistance through complementary ion and charge transfer pathways. As described above, the composite layer 30 adsorbs or desorbs gas molecules to decrease or increase resistance such that the organic electronic multi-sensor may detect a variation for the gas molecules.

Hereinafter, exemplary examples will be described in order to facilitate understanding of the present inventive concept. It should be noted, however, that the following exemplary examples are only for aiding in understanding of the present inventive concept, and the present inventive concept is not limited by the following examples.

PRODUCTION EXAMPLE 1

Preparation of $C_1C_{12}$ IMBr $C_1C_{12}$ IMBr is a material prepared by chemically bonding $C_1C_{12}$, imidazole (IM), and Br. More specifically, 1-methylimidazole ($C_4H_6N_2$) having a methyl group Cl at one side thereof is a precursor. 6 g (73 mmol) of 1-methylimidazole ($C_4H_6N_2$) having a methyl group Cl at one side thereof and 20 g (80.2 mmol) of 1-bromododecane ($C_{12}H_{25}Br$) are dissolved in 80 ml of toluene ($C_7H_8$). The dissolved solution is stirred and reacted in a nitrogen gas atmosphere at a temperature of 110° C. for 72 hours. After the reaction is completed, the solvent is removed by evaporating the yellow reaction mixture, 100 ml of ethyl acetate is added, and then filtering is performed such that 21.5 g of white solid ionic electrolyte $C_1C_{12}$ IMBr is obtained.

PRODUCTION EXAMPLE 2

Preparation of $C_1C_{12}$ IMPF6

$C_1C_{12}$ IMPF6 is a product of the ionic electrolyte prepared by chemically bonding $PF_6$ to $C_1C_{12}$ IMBr using $C_1C_{12}$IMBr prepared through a chemical bonding of Production Example 1 as a precursor. More specifically, $C_1C_{12}$ IMBr (14.4 g and 43.4 mmol) prepared according to Production Example 2 is dissolved in 200 ml of distilled water, 21.25 g (130 mmol) of quaternary ammonium hexafluorophosphate ($NH_4PF_6$) is added, and then stirring is performed at room temperature for 72 hours. After the reaction is completed, the produced solid is filtered and dissolved in chloroform again, and then $MgSO_4$ is added to remove moisture. Further, in order to remove the residual salt or halide starting material, dehydrated dichloromethane is dissolved and kept at a temperature of −30° C. for 24 hours. After 24 hours of storage, 16.2 g of white solid state $C_1C_{12}$ $IMPF_6$ is obtained by filtering the product to remove the solvent therefrom and vacuum drying the product.

PRODUCTION EXAMPLE 3

Fusion of $C_1C_{12}$ $IMPF_6$ with DT-PDPP2T-TT $C_1C_{12}$ $IMPF_6$ is an ionic electrolyte produced according to Production Example 2, and DT-PDPP2T-TT is an organic semiconductor polymer. The ionic electrolyte $C_1C_{12}$ $IMPF_6$ and the organic semiconductor polymer DT-PDPP2T-TT are fused by increasing a volume ratio of the ionic electrolyte $C_1C_{12}$ $IMPF_6$ prepared according to Production Example 2 to the organic semiconductor polymer DT-PDPP2T-TT. For example, the fusion is performed by increasing the volume ratio of the ionic electrolyte $C_1C_{12}$ $IMPF_6$ with respect to the organic semiconductor polymer DT-PDPP2T-TT to 1:1, 1:2, 1:3, 1:5, 1:7, and 1:10. In this time, the ionic electrolyte $C_1C_{12}$ $IMPF_6$ and the organic semiconductor polymer DT-PDPP2T-TT are chemically bonded and fused by being stirred at a temperature of 20° C. to 60° C. for 30 minutes to 2 hours.

PRODUCTION EXAMPLE 4

Formation of Composite Layer

A composite layer is formed of the material fused according to Production Example 3 through a solution process.

A flexible substrate or a rigid substrate is prepared, and the composite layer is formed on the substrate through spin coating. Spin coating is carried out at 2500 rpm for 60 seconds.

Figure 2:
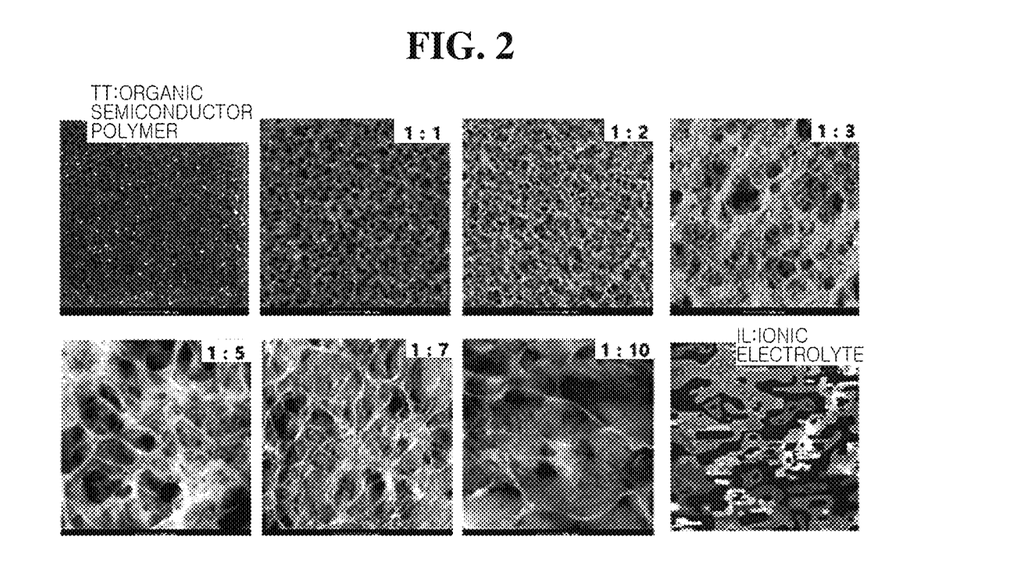
FIG. 2 shows high-angle annular dark-field-scanning/transmission electron microscopy (HADDF-STEM) images for describing an internal shape change of a composite layer according to a fusion volume ratio of an ionic electrolyte to an organic semiconductor polymer in the organic electronic multi-sensor according to one embodiment of the present inventive concept.

FIG. 2 shows high-angle annular dark-field-scanning/transmission electron microscopy (HADDF-STEM) images for describing an internal shape change of a composite layer according to a fusion volume ratio of an ionic electrolyte to an organic semiconductor polymer in the organic electronic multi-sensor according to one embodiment of the present inventive concept.

Referring to FIG. 2, as the fusion volume ratio of the ionic electrolyte is increased, it can be confirmed that the internal mesh shape of the composite layer is varied. The fusion volume ratio is increased to 1:1, 1:2, 1:3, 1:5, 1:7, and 1:10 by increasing the volume ratio of the ionic electrolyte with respect to the organic semiconductor polymer. As the volume ratio of the ionic electrolyte to the organic semiconductor polymer is increased, it can be confirmed that a network having a mesh shape develops. Further, as the volume ratio of the ionic electrolyte to the organic semiconductor polymer is increased, it can be confirmed that a size of a pore between meshes is increased. Furthermore, it can be confirmed that the organic semiconductor polymer exhibits a shape similar to the mesh shapes of the fused example groups.

Figure 3:
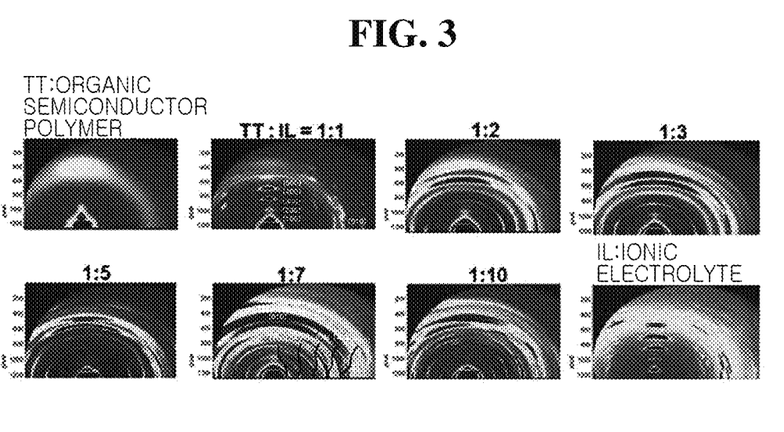
FIG. 3 shows grazing incidence wide angle X-ray scattering images according to the fusion volume ratio of the ionic electrolyte to the organic semiconductor polymer in the organic electronic multi-sensor according to one embodiment of the present inventive concept.

FIG. 3 shows grazing incidence wide angle X-ray scattering (GIWAXs) images according to the fusion volume ratio of the ionic electrolyte to the organic semiconductor polymer in the organic electronic multi-sensor according to one embodiment of the present inventive concept.

Referring to FIG. 3, the GIWAXs images according to the fusion volume ratio are disclosed.

A crystal of the organic electronic multi-sensor may be formed about a (100) crystal face having an ionic electrolyte. As disclosed in the fusion ratio of 1:7 (organic semiconductor polymer 1:ionic electrolyte 7), the organic electronic multi-sensor may have a (010) crystal face, a (200) crystal face, a (300) crystal face, a (400) crystal face, or a (500) crystal face in addition to the (100) crystal face. As a content of the ionic electrolyte to the organic semiconductor polymer is increased, many diffraction points in plane with the substrate are generated. Therefore, it can be seen that a crystal structure is varied according to the fusion ratio.

Figure 4:
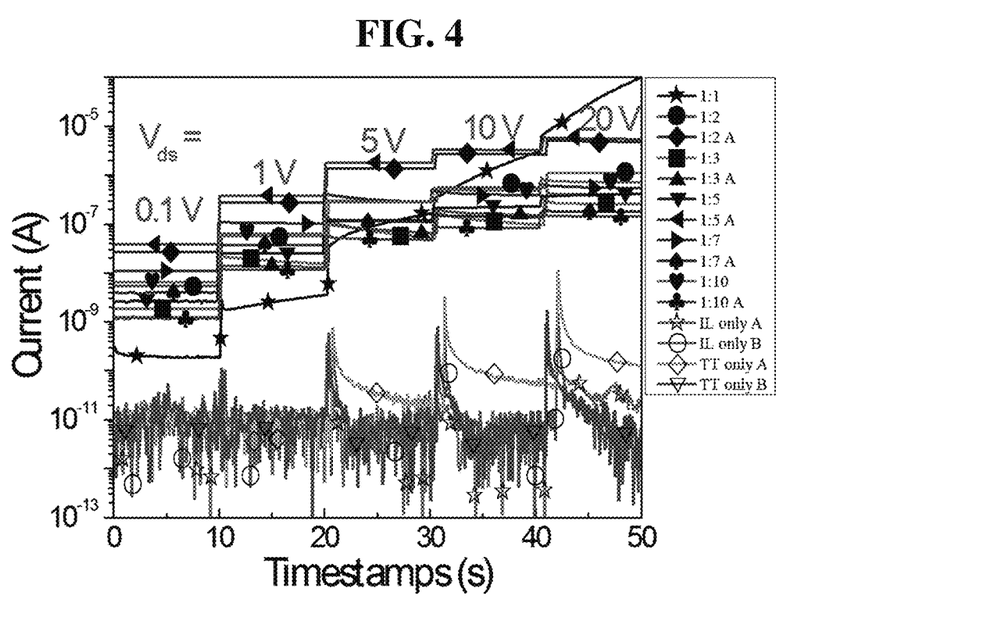
FIG. 4 is a graph showing an electrical characteristic which is varied according to the fusion volume ratio of the ionic electrolyte to the organic semiconductor polymer in the organic electronic multi-sensor according to one embodiment of the present inventive concept.

FIG. 4 is a graph showing an electrical characteristic which is varied according to the fusion volume ratio of the ionic electrolyte to the organic semiconductor polymer in the organic electronic multi-sensor according to one embodiment of the present inventive concept.

FIGS. 4 to 11 are graphs showing analysis results of organic electronic multi-sensors in which the ionic electrolyte is variously fused with the organic semiconductor polymer by increasing the volume ratio of the ionic electrolyte with respect to the organic semiconductor polymer to 1:1, 1:2, 1:3, 1:5, 1:7, and 1:10. For comparison, an analysis result of an organic electronic multi-sensor constituted of only an ionic electrolyte and only an organic semiconductor polymer without fusing the ionic electrolyte material with the organic semiconductor is also included. Further, TT refers to the ionic electrolyte, and IL refers to an organic semiconductor polymer.

Referring to FIG. 4, a voltage-current amount graph of an organic electronic multi-sensor fused by varying a volume ratio of the ionic electrolyte to the organic semiconductor polymer is disclosed. It can be confirmed that the original ionic electrolyte TT and the original organic semiconductor polymer IL, which are not fused with each other, cannot maintain a high current at a low voltage or a high voltage. Thus, it can be seen that a pure material alone cannot be utilized as an organic compound or a multi-sensor. However, when the organic semiconductor polymer and the ionic electrolyte are fused to form a composite layer, it can be confirmed that a current of $10^{-7}$ A to $10^{-9}$ A is maintained at a low voltage of 0.1 V. Further, it can be confirmed that as the voltage is gradually increased, the current is also increased gradually. However, there is a slight difference in current according to the content of the ionic electrolyte fused with the organic semiconductor polymer. This is confirmed in the HAADF-STEM and GIWAXs images shown in FIGS. 2 to 3, and this data shows a difference in electrical characteristic due to variations in mesh structure and crystal structure.

Figure 5:
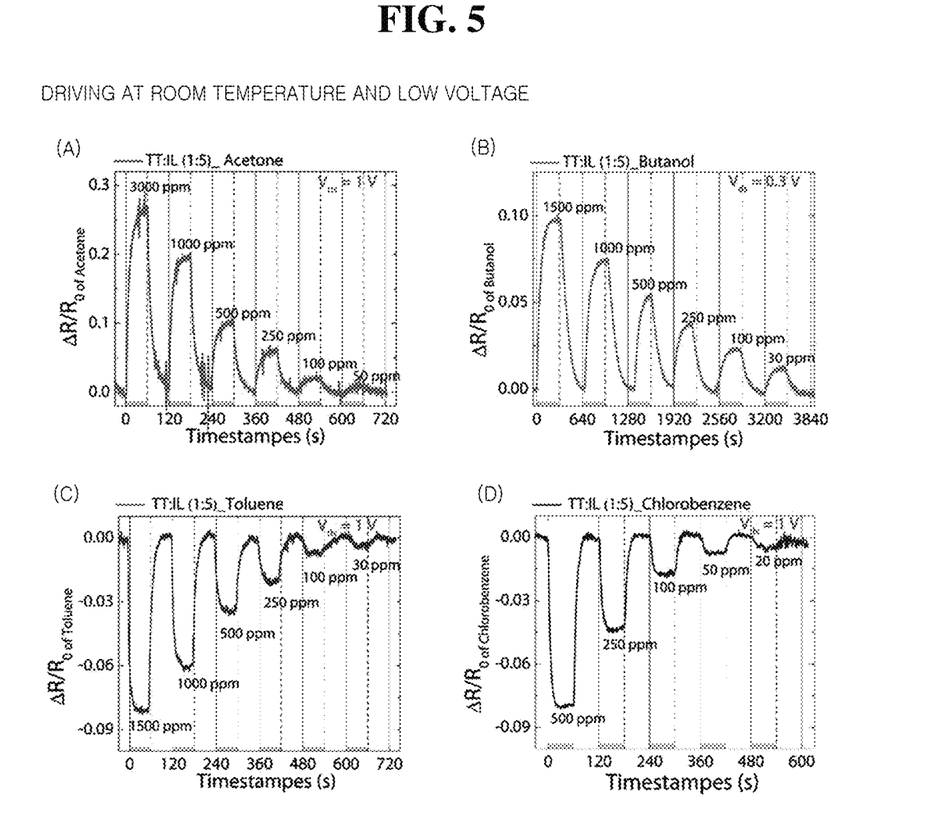
FIG. 5 shows graphs showing characteristics of adsorption performance of the organic electronic multi-sensor according to one embodiment of the present inventive concept, which is driven at room temperature and a low voltage, with respect to polarity and non-polar volatile organic compounds.

FIG. 5 shows graphs showing characteristics of adsorption performance of the organic electronic multi-sensor according to one embodiment of the present inventive concept, which is driven at room temperature and a low voltage, with respect to polarity and non-polar volatile organic compounds.

Referring to FIG. 5, the organic electronic multi-sensor is produced with a fusion volume ratio 1:5. FIG. 5A illustrates a graph showing absorption performance for acetone, FIG. 5B illustrates a graph showing absorption performance for butanol, FIG. 5C illustrates a graph showing absorption performance for toluene, and FIG. 5D illustrates a graph showing absorption performance for chlorobenzene.

It can be confirmed that various volatile organic compounds are detected in a low voltage (0.3 V or 1 V) state at room temperature without an additional heating device. It can be confirmed that the driven organic electronic multi-sensor is excellent in adsorption performance of the volatile organic compound even at a low voltage at room temperature in comparison with a state in which driving of the organic electronic multi-sensor is stopped. It can be confirmed that resistance increases in the case of polar volatile organic compounds (acetone and butanol), and resistance decreases in the case of non-polar volatile organic compounds (toluene and, chlorobenzene). Therefore, it can be confirmed that the organic electronic multi-sensor distinguishes the polarities of the volatile organic compounds.

Figure 6:
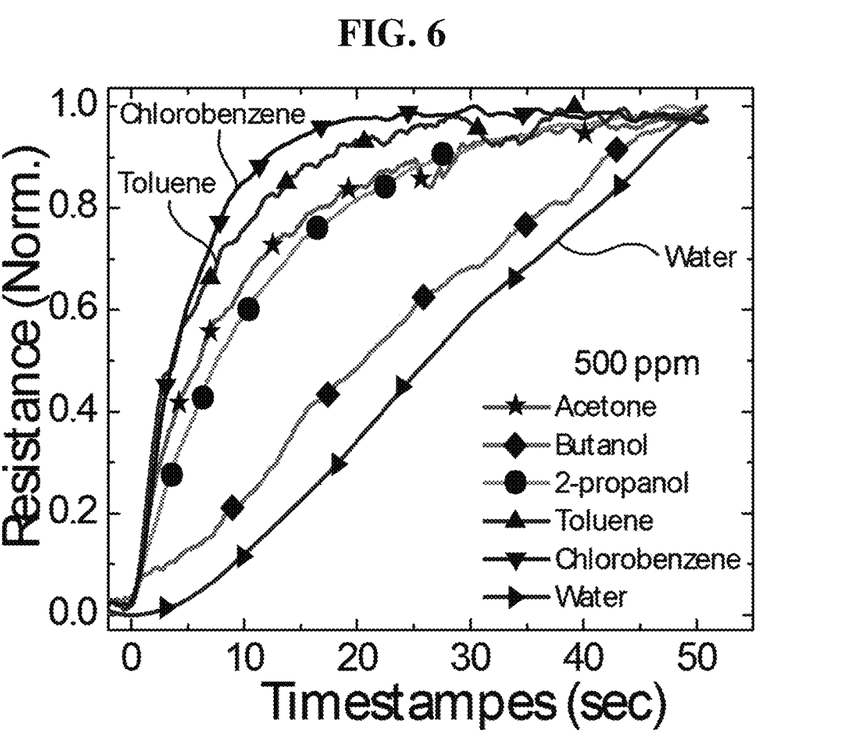
FIG. 6 is a graph showing a characteristic of a response speed of the organic electronic multi-sensor according to one embodiment of the present inventive concept, which is driven at room temperature and a low voltage, with respect to polarity and non-polar volatile organic compounds.

FIG. 6 is a graph showing a characteristic of a response speed of the organic electronic multi-sensor according to one embodiment of the present inventive concept, which is driven at room temperature and a low voltage, with respect to polarity and non-polar volatile organic compounds.

Referring to FIG. 6, a graph showing normalization of reaction rates of the organic electronic multi-sensor driven at room temperature and a low voltage for various volatile organic compounds is disclosed. The organic electronic multi-sensor has different reaction rates according to polarities of the volatile organic compounds, and this means that signal transfer processes of the organic electronic multi-sensor are different according to polarity characteristics.

Figure 7:
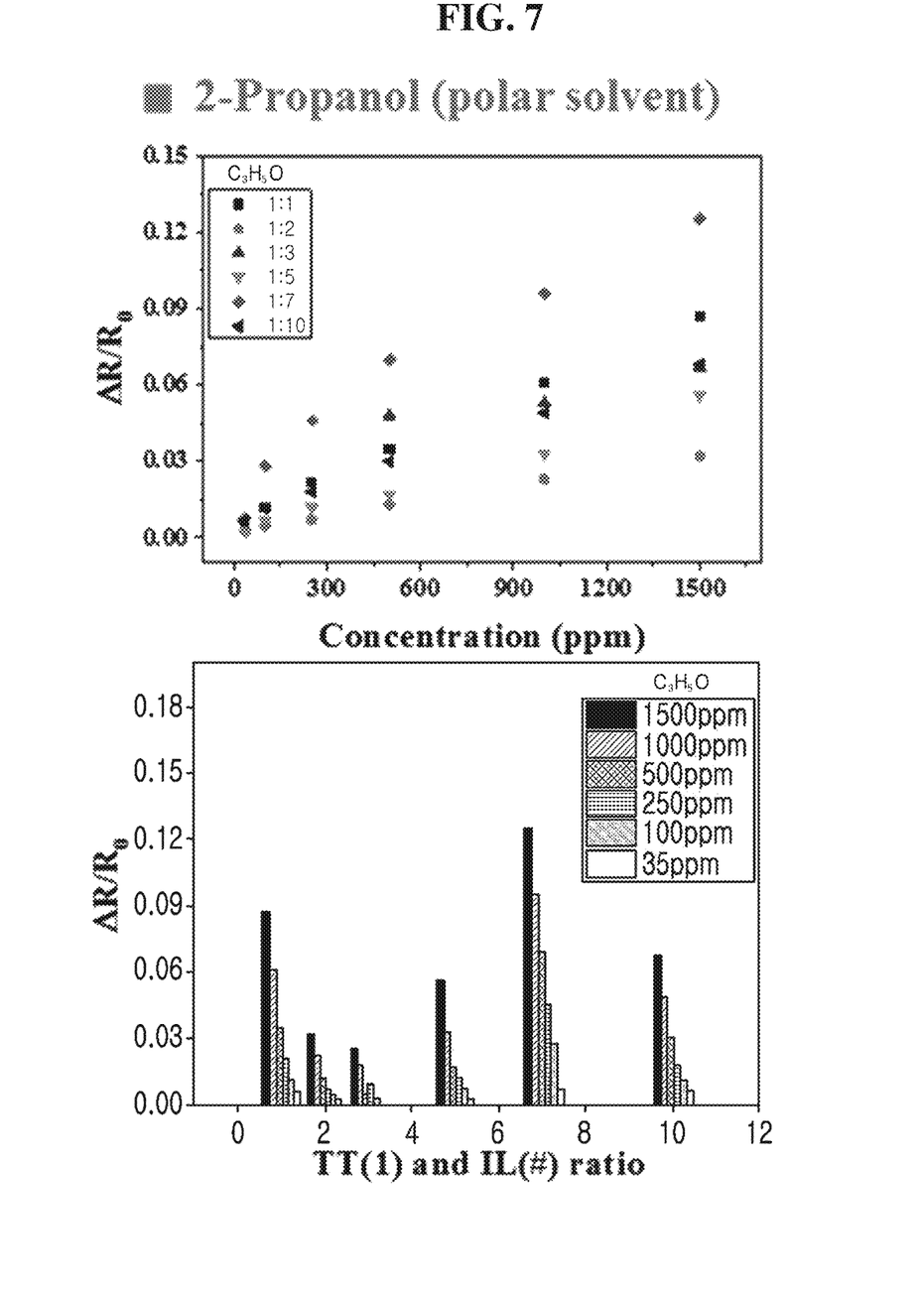
FIGS. 7 and 8 are graphs showing a characteristic of adsorption performance of the organic electronic multi-sensor according to one embodiment of the present inventive concept with respect to polar organic compounds.
Figure 8:
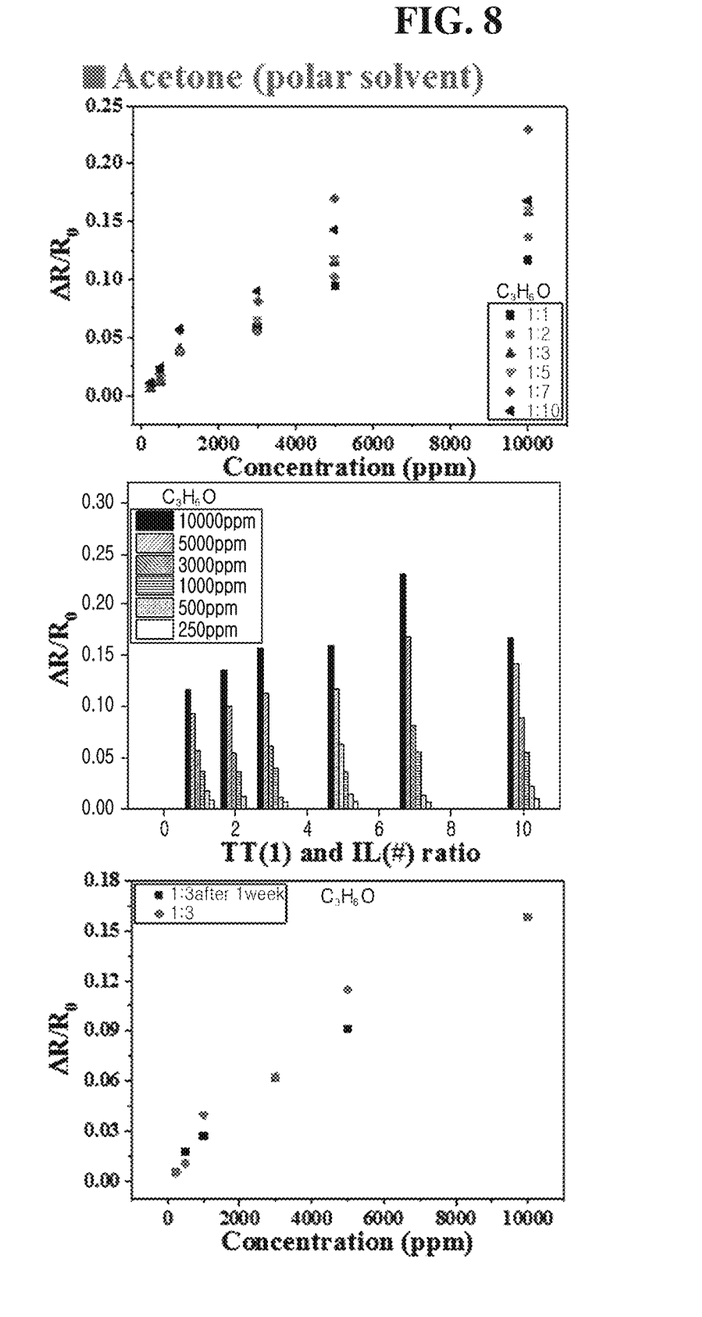

FIGS. 7 and 8 are graphs showing a characteristic of adsorption performance of the organic electronic multi-sensor according to one embodiment of the present inventive concept with respect to polar organic compounds.

Referring to FIG. 7, according to a characteristic graph of adsorption performance for the volatile organic compound, e.g., isopropyl alcohol (IPA), a variation in resistance according to a concentration of IPA and the fusion ratio of the ionic electrolyte to the organic semiconductor can be confirmed. It can be seen that the volatile organic compounds are sensed through an increase of the resistance of the organic electronic multi-sensor.

FIG. 8 is a graph showing a characteristic of adsorption performance for a volatile organic compound, e.g., acetone, and a variation in resistance according to a fusion ratio of the ionic electrolyte to the organic semiconductor and a concentration of acetone can be confirmed. Further, even after the organic electronic multi-sensor produced with 1:3 of a fusion ratio of the organic semiconductor to the ionic electrolyte is exposed in air for one week, it can be confirmed that the adsorption performance for acetone is maintained.

As described above, a variation value according to the concentrations and the fusion volume ratio of IPA and acetone, which are polar solvents, refers to the adsorption performance of the organic electronic multi-sensor for IPA and acetone, which are the polar solvents, and it can be confirmed that resistance values of a Y-axis of IPA and acetone, which are polar organic compound gases, decrease. In particular, in the case of an organic electronic multi-sensor fused with 1:7 of a volume ration of the organic semiconductor polymer to the ionic electrolyte, the resistance value exhibited a most reduced value. Therefore, it can be confirmed that when IPA and acetone among polar organic compound gases are fused with a volume ratio of 1:7, the adsorption performance of the organic electronic multi-sensor is most excellent.

Figure 9:
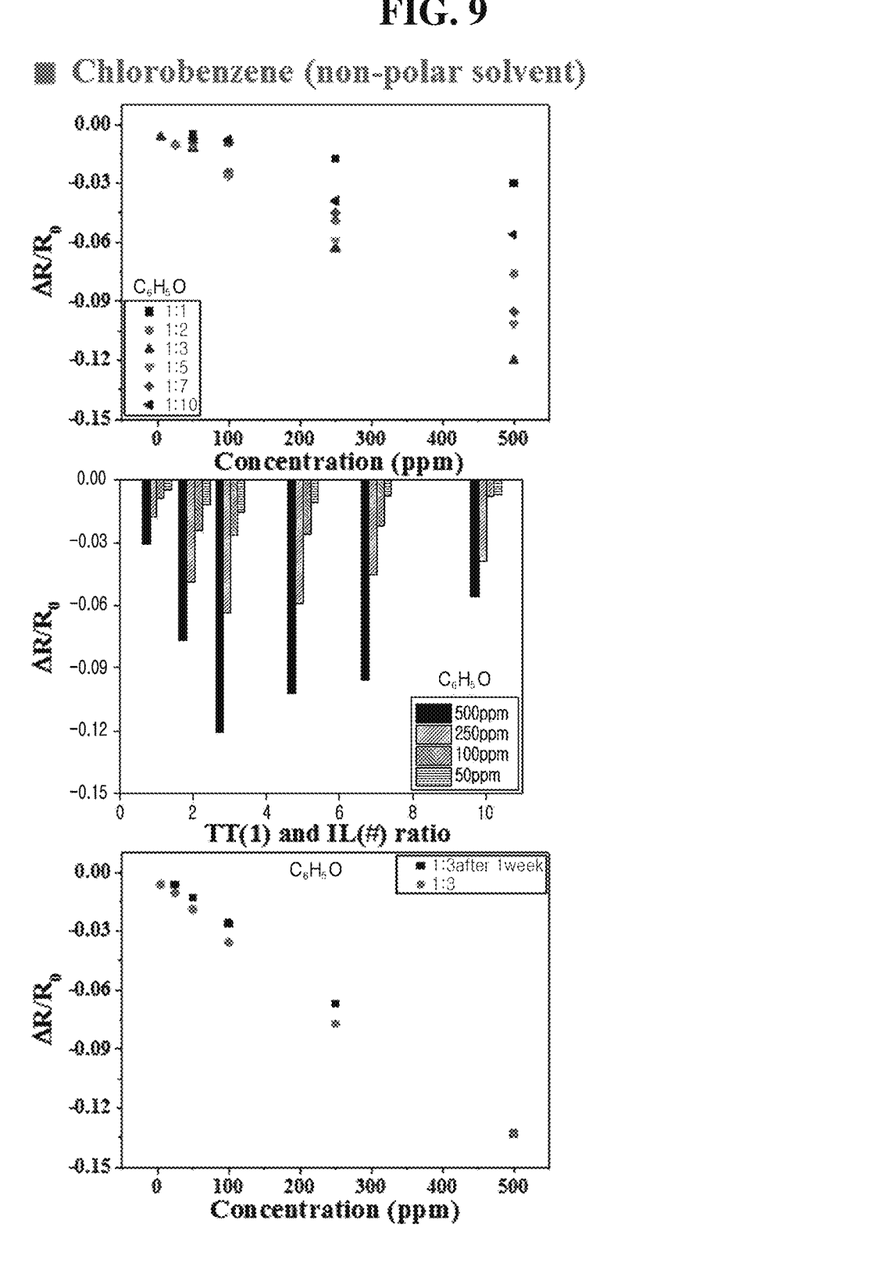
FIGS. 9 and 10 are graphs showing a characteristic of adsorption performance of the organic electronic multi-sensor according to one embodiment of the present inventive concept with respect to non-polar organic compounds.
Figure 10:
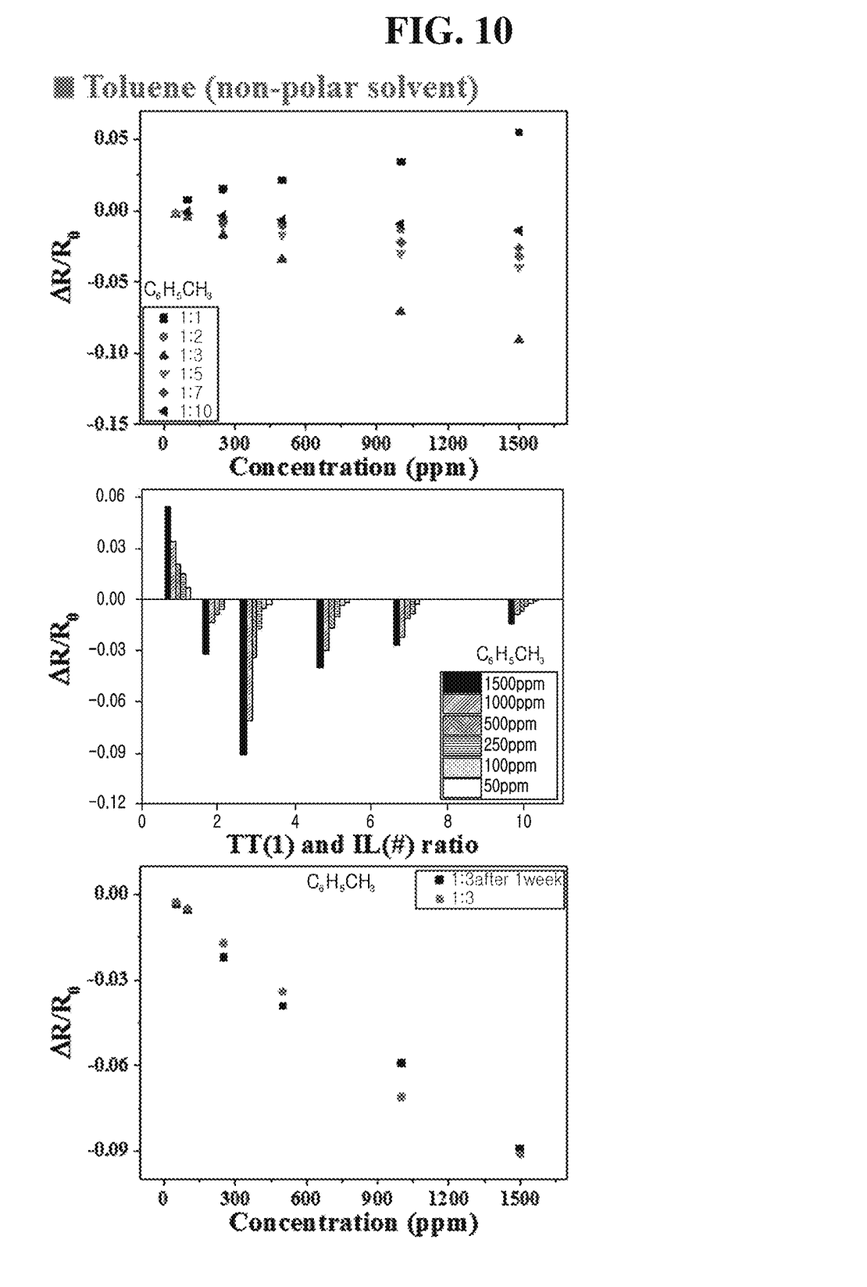

FIGS. 9 and 10 are graphs showing a characteristic of adsorption performance of the organic electronic multi-sensor according to one embodiment of the present inventive concept with respect to non-polar organic compounds.

Referring to FIG. 9, adsorption performance of the organic electronic multi-sensor for a volatile organic compound, e.g., chlorobenzene, through a variation in resistance, wherein the adsorption performance is varied according to a concentration and a fusion ratio can be confirmed. Further, after the organic electronic multi-sensor fused with 1:3 of a fusion ratio of the organic semiconductor to the ionic electrolyte is exposed in air for one week, a variation in resistance can be confirmed.

Referring to FIG. 10, adsorption performance of the organic electronic multi-sensor for a volatile organic compound, e.g., toluene, through a variation in resistance, wherein the adsorption performance is varied according to a concentration and a fusion ratio can be confirmed. Further, after the organic electronic multi-sensor fused with 1:3 of a fusion ratio of the organic semiconductor to the ionic electrolyte is exposed in air for one week, a variation in resistance can be confirmed.

As described above, a variation value according to the concentrations and the fusion volume of chlorobenzene and toluene which are non-polar solvents refers to the adsorption performance of the organic electronic multi-sensor for chlorobenzene and toluene which are non-polar solvents. Further, in the case of the non-polar organic compound gas, it can be confirmed that the resistance value of the Y-axis increases. As described above, through a decrease or an increase of the resistance of the organic electronic multi-sensor, the volatile organic compound may be distinguished from the polar organic compound or the non-polar organic compound.

Consequently, according to a variation in volume ratio of the ionic electrolyte fused with the organic semiconductor polymer, an electrical characteristic and gas adsorption performance of the organic electronic multi-sensor may be improved.

Further, the volume ratio of the ionic electrolyte to the organic semiconductor polymer is increased, and a modification is made to the shape of the organic electrolyte layer such that the characteristic of adsorption performance of the organic electronic multi-sensor for the organic compound may be controlled.

Figure 11:
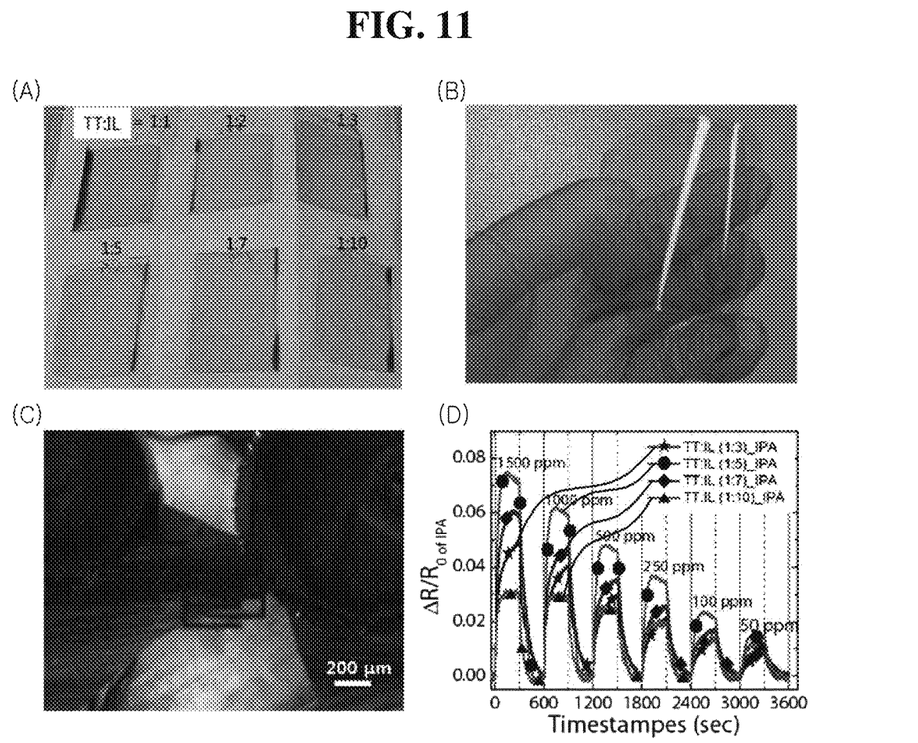
FIG. 11 shows images of an organic electronic multi-sensor according to one embodiment of the present inventive concept and a graph showing a characteristic of adsorption performance of the organic electronic multi-sensor formed on a flexible substrate.

FIG. 11 shows images of an organic electronic multi-sensor according to one embodiment of the present inventive concept and a graph showing a characteristic of adsorption performance of the organic electronic multi-sensor formed on a flexible substrate.

Referring to FIG. 11, FIGS. 11A to 11C show a potential of large-area printing according to a variation in the volume ratio of the organic electrolyte fused with the organic semiconductor polymer. In addition, it demonstrates that large-area printing is possible on a flexible substrate such as PET or the like, and it can be seen that mechanical flexibility is also excellent. A crystal domain and a crystal grain boundary may be observed through polarized optical microscopy, and this is because of a characteristic of a crystal structure of the organic electrolyte. Further, as shown in a graph of FIG. 11D, even though the organic electronic multi-sensor of the present inventive concept is a two terminal-based small device without a gate, it can be confirmed that the organic electronic multi-sensor of the present inventive concept has excellent adsorption performance for the volatile organic compound (IPA).

Figure 12:
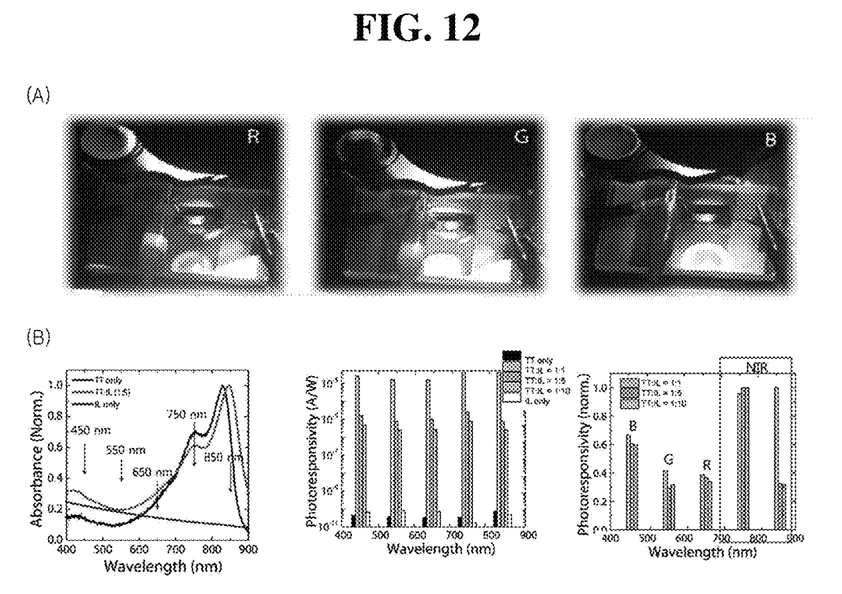
FIG. 12 shows images and graphs showing a characteristic of a light reaction according to a wavelength in the organic electronic multi-sensor according to one embodiment of the present inventive concept.

FIG. 12 shows images and graphs showing a characteristic of a light reaction according to a wavelength in the organic electronic multi-sensor according to one embodiment of the present inventive concept.

Referring to FIG. 12, FIG. 12A shows images capturing irradiation of light in the range of various wavelengths, and FIG. 12B shows graphs reference showing characteristics of light reaction. It can be seen that the organic semiconductor polymer exhibits a wide absorption spectrum in the range of 400 nm to 900 nm, but the organic electrolyte hardly absorbs light. Therefore, it can be confirmed that a characteristic of light reaction of the organic electronic multi-sensor having 1:5 of a volume ratio of the organic electrolyte to the organic semiconductor polymer depends entirely on the absorption characteristic of the organic semiconductor polymer.

As a result of the characteristic of light reaction by irradiating light in the range of various wavelengths, it can be seen that characteristics of light reaction of a single organic semiconductor polymer and the organic electrolyte were hardly observed, but in the case of composite layers fused with a ratio of 1:1, 1:5, and 1:10, very high characteristics of light reaction were exhibited. In particular, it can be seen that a characteristic of light reaction of a layer fused with a ratio of 1:1 is increased up to $10^8$ times for each wavelength.

As a result of comparing normalized light reactivity for each wavelength, a range showing maximum light reactivity is an NIR range (700 nm to 900 nm), and this result is accurately consistent with the absorption data. However, it can be seen that, as an amount of the organic electrolyte is increased, the light reactivity is degraded. This is because a content of the organic semiconductor polymer is relatively decreased.

Figure 13:
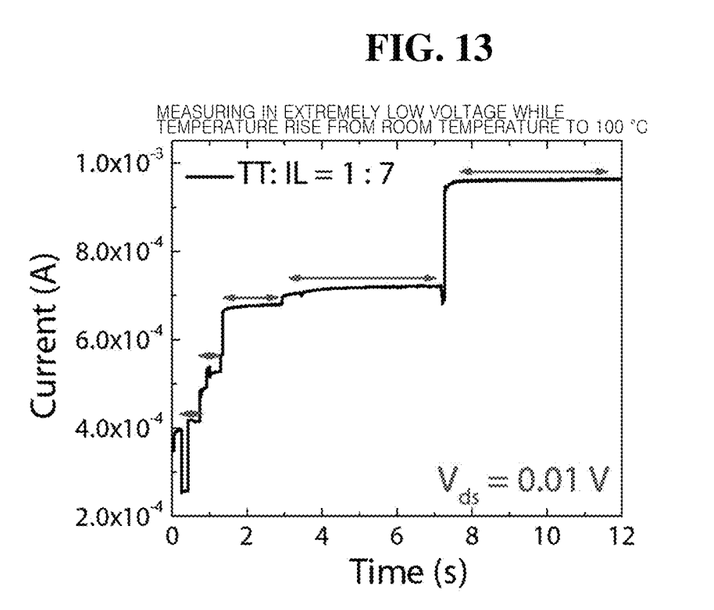
FIG. 13 is a graph showing analysis of a characteristic of a variation in resistance due to a temperature of the organic electronic multi-sensor according to one embodiment of the present inventive concept.

FIG. 13 is a graph showing analysis of a characteristic of a variation in resistance due to a temperature of the organic electronic multi-sensor according to one embodiment of the present inventive concept.

Referring to FIG. 13, a graph of a variation in current is shown at an extremely low voltage of 0.01 V while increasing a temperature of the organic electronic multi-sensor in which the organic semiconductor polymer and the organic electrolyte are fused with a ratio of 1:7 from room temperature to a temperature of 100° C. It can be seen that, as the temperature rises, the current increases very rapidly, and a region in which a current is saturated occurs in each section. This is because as the temperature rises, a crystal structure of the organic electrolyte is varied such that ionic conductivity is changed.

The organic electronic multi-sensor has a two-terminal structure not requiring a gate electrode and can be driven at room temperature and a low voltage such that process stability can be increased due to not requiring an additional heating device, and a production cost of a process can also be reduced. Further, the organic electronic multi-sensor of the present inventive concept can implement a characteristic of low consumption power even on a flexible PET substrate, thereby having high economic feasibility as a next-generation wearable electronic device.

The invention claimed is:

1. An organic electronic multi-sensor comprising:
   a substrate;
   a composite layer formed on the substrate and including an ionic electrolyte and an organic semiconductor polymer; and
   a source electrode layer and a drain electrode layer formed on both sides of the composite layer and electrically connected to the composite layer,
   wherein the ionic electrolyte is dissolved in a non-polar solvent and contains a plurality of alkyl groups,
   the ionic electrolyte is doped with the organic semiconductor polymer by electrostatic attraction of the ionic electrolyte, and
   the composite layer adsorbs or desorbs gas molecules according to a chemical signal by fusing the ionic electrolyte with the organic semiconductor polymer, detects light per wavelength according to an optical signal, or detects an environmental change by converting a temperature into an electrical signal according to a thermal signal.

2. The organic electronic multi-sensor of claim 1, wherein the substrate includes a polyethylene terephthalate (PET) substrate having a flexible property.

3. The organic electronic multi-sensor of claim 1, wherein a precursor of the ionic electrolyte includes 1-methylimidazole, 1-alkyl-3alkyl-imidazolium, n-dialkyl-pyrrolidinium, 1,2-dialkyl-pyrazolum, n-alkyl-thiazolium, n-alkyl-pyridinium, n-diakyl-piperidinium, tetraalkyl-ammomium, tetraalkyl-phosphonium, or trialkyl-sulfonium.

4. The organic electronic multi-sensor of claim 1, wherein the ionic electrolyte contains an alkyl group with carbon numbers 1 to 12.

5. The organic electronic multi-sensor of claim 1, wherein the ionic electrolyte is either solid or liquid.

6. The organic electronic multi-sensor of claim 1, wherein the ionic electrolyte includes an anionic material selected from among PF6, NTf2, BR1R2R3R4, BF4, OTf2, N(CN)2, CH3CO2, CF3CO2NO3, Br, Cl, and I.

7. The organic electronic multi-sensor of claim 1, wherein the organic semiconductor polymer includes a polymer, in which a double bond and a single bond are alternated, selected from among thiophene, fused thiophene, carbazole, benzodithiozole, diketopyrrolopyrrole, and indacenodithiophene.

8. The organic electronic multi-sensor of claim 1, wherein the composite layer is fused with a volume ratio of 1:1, 1:2, 1:3, 1:5, 1:7, or 1:10 by increasing the volume ratio of the ionic electrolyte with respect to the organic semiconductor polymer.

9. The organic electronic multi-sensor of claim 1, wherein the ionic electrolyte and the organic semiconductor polymer of the composite layer simultaneously have different ion and charge transfer systems or have complementary ion and charge transfer systems.

10. The organic electronic multi-sensor of claim 1, wherein the composite layer is formed with a double layer by fusing the ionic electrolyte with the organic semiconductor polymer and has a mesh shape.

11. A method of producing an organic electronic multi-sensor which includes a substrate, a composite layer formed on the substrate and including an ionic electrolyte and an organic semiconductor polymer, and a source electrode layer and a drain electrode layer formed on both sides of the composite layer and electrically connected to the composite layer, wherein the ionic electrolyte is dissolved in a non-polar solvent and contains a plurality of alkyl groups, the ionic electrolyte is doped with the organic semiconductor polymer by electrostatic attraction of the ionic electrolyte, and the composite layer adsorbs or desorbs gas molecules according to a chemical signal by fusing the ionic electrolyte with the organic semiconductor polymer, detects light per wavelength according to an optical signal, or detects an environmental change by converting a temperature into an electrical signal according to a thermal signal, the method comprising:

preparing a precursor of the ionic electrolyte;

introducing a functional group into the precursor so as to allow the precursor to be soluble in the non-polar solvent;

preparing the ionic electrolyte by chemically bonding the precursor in which the functional group is introduced to an anionic salt; and forming the composite layer by fusing the prepared ionic electrolyte with the organic semiconductor polymer.

12. The method of claim 11, wherein, in the preparing of the precursor, the precursor of the ionic electrolyte includes 1-methylimidazole, 1-alkyl-3alkyl-imidazolium, n-dialkyl-pyrrolidinium, 1,2-dialkyl-pyrazolum, n-alkyl-thiazolium, n-alkyl-pyridinium, n-diakyl-piperidinium, tetraalkyl-ammomium, tetraalkyl-phosphonium, or trialkyl-sulfonium.

13. The method of claim 11, wherein, in the preparing the ionic electrolyte, the anionic salt includes an anionic material selected from among $PF_6$, $NTf_2$, $BR_1R_2R_3R_4$, $BF_4$, $OTf_2$, $N(CN)_2$, $CH_3CO_2$, $CF_3CO_2NO_3$, Br, Cl, and I.

14. The method of claim 11, wherein, in the preparing of the ionic, the prepared ionic electrolyte is in a solid or liquid state.

15. The method of claim 11, wherein, in the forming of the composite layer, the composite layer is fused with a volume ratio of 1:1, 1:2, 1:3, 1:5, 1:7, or 1:10 by increasing the volume ratio of the ionic electrolyte with respect to the organic semiconductor polymer.

16. The method of claim 11, wherein, in the forming of the composite layer, the ionic electrolyte and the organic semiconductor are fused to form a double layer, and the double layer has a mesh shape.

17. The method of claim 11, wherein the ionic electrolyte is either solid or liquid.

* * * * *